US00PP20295P2

(12) United States Plant Patent
Zaiger et al.

(10) Patent No.: US PP20,295 P2
(45) Date of Patent: Sep. 15, 2009

(54) INTERSPECIFIC ALMOND TREE NAMED 'ALM-21'

(50) Latin Name: *Prunus dulciss×Prunus persica*
Varietal Denomination: Alm-21

(76) Inventors: Gary Neil Zaiger, 1908 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 11 days.

(21) Appl. No.: 12/152,618

(22) Filed: May 16, 2008

(51) Int. Cl.
*A01H 5/00* (2006.01)

(52) U.S. Cl. ..... Plt./155
(58) Field of Classification Search ..... Plt./155
See application file for complete search history.

*Primary Examiner*—Susan B McCormick Ewoldt

(57) ABSTRACT

A new and distinct variety of Interspecific Almond tree. The following features of the tree and its nuts are characterized with the tree budded on 'Nemaguard' Rootstock (non-patented), grown on Handford sandy loam soil with Storie Index rating 95, in USDA Hardiness Zone 9, near Modesto, Calif., with standard commercial almond growing practices, such as pruning, spraying, irrigation and fertilization. Its novelty consist of the following combination of desirable features:

1. The tree being self fertile with the ability to produce almonds without the use of pollinators.
2. Vigorous, upright growth of the tree.
3. Producing nuts that are well sealed and soft shelled.
4. Nuts having very good eating quality.
5. Nuts harvesting 7 to 10 days before 'Nonpariel' Almond (non-patented).
6. The pollen being compatible with 'Nonpariel' Almond (non-patented) and blooming in the same blooming season.

1 Drawing Sheet

Botanical classification: *Prunus* species.

BACKGROUND OF THE VARIETY

Field of the Invention

In the field of plant genetics, we conduct an extensive and continuing plant-breeding program including the organization and asexual reproduction of orchard trees, and of which almonds, plum, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of almond trees, which are known to us, and mentioned herein, 'All-in One' (U.S. Plant Pat. No. 4,304), 'Nonpariel' (non-patented) and the proprietary almond seedling '21G8'.

ORIGIN OF THE VARIETY

The new and distinct Interspecific almond tree [(*Prunus dulcis*×*Prunus persica*)×*Prunus dulcis*] was originated by us in our experimental orchard located near Modesto, Calif. as a first generation cross between 'All-in-One' Almond (U.S. Plant Pat. No. 4,304) and the proprietary almond seedling with the field identification number '21G8'. The pollen parent (21G8) originated as a volunteer almond seedling growing in our experimental orchard where almond crosses had been planted in previous years. A large group of seedlings from this first generation cross were planted and grown on their own root system in our experimental orchard located near Modesto, Calif. Under close and careful observation, one such seedling, which is the present variety, exhibited desirable nut and tree characteristics and, in 2001, was selected for asexual propagation and commercialization.

ASEXUAL REPRODUCTION OF THE VARIETY

Asexual reproduction of the new and distinct variety of interspecific almond tree was by budding to 'Nemaguard' Rootstock (non-patented), as performed by us in our experimental orchard located near Modesto, Calif. and shows that reproductions run true to the original tree and all characteristics of the tree and its nuts are established and transmitted through succeeding asexual propagations.

SUMMARY OF THE NEW VARIETY

The new and distinct interspecific almond tree, [(Almond×Peach)×Almond)], is of large size, vigorous, upright growth and a productive and regular bearer of soft shell nuts with kernels having an excellent flavor similar to 'Nonpariel' Almond (non-patented). The harvest maturity for knocking, (shaking the nuts from the tree), is approximately one week before our leading almond variety 'Nonpariel' Almond (non-patented) and the nuts release from the tree readily. The soft shell of the nut is well sealed, readily hulled and shelled, similar to 'Nonpariel' Almond (non-patented). The low percentage of doubles, usually less than 10% under growing conditions prevailing in our area, Stanislaus County, Calif. The primary difference between the new variety and 'Nonpariel' Almond (non-patented) is the new variety is self fertile and 'Nonpariel' Almond (non-patented) is self sterile and needs a pollinator tree planted near to fertilize the flowers to produce almonds. In comparison to its seed parent 'All-in-One' Almond (U.S. Plant Pat. No. 4,304), the new variety blooms earlier by 8–10 days and matures earlier by approximately one week. In comparison to its pollen parent (21G8), the new variety has nuts with soft shells compared to a hard shells and blooms earlier by approximately 10–14 days.

PHOTOGRAPH OF THE VARIETY

The accompanying color photographic illustration shows typical specimens of the flowers, foliage and nuts of the present new interspecific almond variety at 5 years of age. The illustration shows a typical flower inset, the upper and lower surface of the leaves, a spur with a cluster of nuts, hulls are shown with one green immature hull from the growing period and several nuts with mature hulls showing the splitting, dried, light brown condition at harvest time, two individual nuts are shown without hulls and three kernels are shown without shells. The photographic illustration was taken shortly after being harvested and the colors are as nearly true as is reasonably possible in a color representation of this type.

DESCRIPTION OF THE VARIETY

The following is a detailed botanical description of the new variety of interspecific almond tree, its flowers, foliage and nuts, as based on observations of 5 year old specimens grown near Modesto, Calif., with color in accordance with Munsell Book of Color.

Tree:

*Size.*—Large, normal for commercial almond trees. Height approximately 4 meters, width 3 meters, varies slightly with type and fertility of soil.

*Vigor.*—Vigorous, tree growth of 1.5 to 2 meters the first growing season.

*Form.*—Upright, slightly more upright than 'Nonpariel' Almond (non-patented).

*Branching Habit.*—Upright, crotch angle approximately 40°, increases with heavy crop load.

*Productivity.*—Productive, comparable to 'Nonpariel' Almond (non-patented) in crop load. Varies with type and fertility of soil.

*Bearer.*—Regular, heavy crop load 3 consecutive years, no alternate bearing observed.

*Fertility.*—Self fertile.

*Density.*—Medium dense, usually pruned to open center of tree allowing more sunlight to enhance health of nut bearing spurs.

*Hardiness.*—Hardy in all almond growing areas of California. Tree grown in USDA Hardiness Zone 9. Winter chilling requirement similar to that of 'Nonpariel' Almond (non-patented) and blooming during the same blooming period in our experimental orchard.

Trunk:

*Size.*—Medium stocky. Average circumference 58.4 cm at 25.4 cm above ground on a 5 year old tree.

*Stocky.*—Medium stocky.

*Texture.*—Medium shaggy, becoming rougher with age.

*Color.*—Varies from 10YR 3/4 to 2.5Y 6/2.

Branches:

*Size.*—Medium, normal for almond trees. Average circumference 22.4 cm at 1 meter above ground.

*Surface texture.*—New growth smooth, varies to medium rough with age.

*Lenticels.*—Average number 121 in a 25.8 square cm area. Average length 2.3 mm. Average width 0.9 mm. Color varies from 7.5YR 6/10 to 10YR 6/8.

*Color.*—New growth varies from 5GY 6/6 to 5GY 5/6. Old growth varies from 7.5YR 3/4 to 10YR 4/2, becomes darker with age.

Leaves:

*Size.*—Small to medium. Average length 82.3 mm. Average width 25.8 mm.

*Form.*—Lanceolate.

*Apex.*—Acuminate.

*Base.*—Cuneate.

*Margin.*—Crenulate.

*Thickness.*—Medium, normal for almonds.

*Surface texture.*—Upper surface relatively smooth, very slight indentations over midrib and leaf veins. Lower surface relatively smooth with very small ridges created by midrib and pinnate venation. Both surfaces glabrous.

*Petiole.*—Average length 24.5 mm. Average width 1.4 mm. Color varies from 5GY 7/6 to 5GY 6/6. Longitudinally grooved. Upper and lower surfaces glabrous.

*Glands.*—Type — globose. Size — small. Average length 0.6 mm. Average diameter 0.4 mm. Number varies from 4 to 6, average 5. Located on upper portion of petiole and base of leaf blade. Color varies from 5GY 8/4 to 5GY 7/6.

*Color.*—Upper surface varies from 5GY 4/4 to 5GY 4/8. Lower surface varies from 5GY 4/4 to 5GY 4/6. Midvein color varies from 5GY 9/4 to 5GY 8/4.

*Venation.*—Pinnately veined.

*Stipules.*—Typically 2 per leaf bud with up to 8 per shoot tip. Average length 4.5 mm. Form — lanceolate with a serrated margin. Color varies from 2.5GY 5/6 to 5GY 5/8.

Flower buds:

*Size.*—Large. Average length 17.7 mm. Average diameter 7.9 mm.

*Hardiness.*—Hardy in all almond growing areas of California.

*Form.*—Elongated.

*Pedicel.*—Average length 4.6 mm. Average width 2.1 mm. Color varies from 5GY 7/8 to 5GY 6/6.

*Color.*—Varies from 5RP 9/2 to 7.5RP 9/2.

*Number of buds per spur.*—Average number 3.

Flowers:

*Size.*—Large. Average height 18.3 mm. Average diameter 37.7 mm.

*Petals.*—Normally five, alternately arranged to sepals. Obovate, apex undulated, base narrows at point of attachment. Average length 20.6 mm. Average width 14.1 mm. Margin, sides entire. Upper and lower surfaces glabrous. Color varies from 5RP 9/2 to N 9.5/ (white).

*Sepals.*—Normally 5, alternately arranged to petals. Shape, triangular, apex rounded. Average length 8.7 mm. Average width 4.9 mm. Margin — entire. Upper surface glabrous, lower surface pubescent. Color — upper surface varies from 2.5GY 6/8 to 5GY 6/6. Lower surface varies from 7.5R 2/8 to 5GY 5/6.

*Stamens.*—Average number per flower 37. Average filament length 10.0 mm. Filament color N 9.5/ (white). Anther color varies from 5Y 8.5/10 to 5Y 8/10.

*Pollen.*—Self fertile. Color varies from 5Y 8/10 to 5Y 7/10.

*Pistil.*—Normally one. Surface pubescent. Average length 14.4 mm. Position of stigma to anthers relatively even. Color varies from 2.5GY 9/4 to 5GY 8/4.

*Fragrance.*—Slight.

*Blooming period.*—Same blooming season as 'Nonpariel' Almond (non-patented). Date of First Bloom Feb. 16, 2005. Date of Petal Fall Feb. 28, 2005, varies slightly with climatic conditions.

*Number flowers per flower bud.*—One.

*Pedicel.*—Average length 5.4 mm. Average width 2.1 mm. Color varies from 2.5GY 6/6 to 5GY 7/6.

*Color.*—Varies from 5RP 9/2 to N 9.5/ (white).

Nut crop:

*Productivity.*—Very heavy, beginning in 3$^{rd}$ leaf.

*Maturity when described.*—Hull split, when abscission layer formed between spur and nuts.

*Date of harvest period.*—August 7–20, varies slightly with climatic conditions. Approximately 1 to 10 days before 'Nonpariel' Almond (non-patented) harvest.

*Distribution.*—Well distributed throughout the tree.

*Tenacity.*—Hangs well until harvest time.

Hull:

*Surface.*—Relatively smooth, short pubescence.

*Form.*—Elliptical.

*Thickness.*—Average 2.0 mm when dry.

*Flesh.*—Leathery, becomes brittle when dry.

*Suture.*—Minimal, relatively smooth.

*Color.*—Varies from 7.5Y 7/4 to 7.5Y 7/6 during growing season. Varies from 7.5RP 4/2 to 10RP 5/2 when dry.

*Dehiscence.*—Good, opens freely, splitting along suture.

*Nut cavity.*—Oval.

*Adherence.*—Hulls easily removed from nuts by mechanical huller.

Shell:

*Size.*—Large. Average length 32.7 mm. Average width 20.2 mm. Average thickness 12.9 mm.

*Shape.*—Elongated, ovate.

*Thickness.*—Classified as paper shell, (i.e. easy to crack).

*Color.*—Outer color varies from 10YR 8/6 to 10YR 7/6. Inner color varies from 10YR 6/6 to 2.5Y 8/4.

*Surface.*—Outer surface covered with randomly spaced small, shallow, round pits. One very small, shallow, long groove on each side of the well sealed suture, extending from base to apex. Inner surface covering the kernel is smooth. Shell easily removed from kernel by mechanical sheller.

*Apex.*—Pointed, acuminate. Average length 0.7 mm.

*Base.*—Flat.

*Stem scar.* —Large in size. Wing— thin, extends from base to apex. Percent of kernel to nut, approximately 60%.

Kernel:

*Size.*—Large. Average length 24.9 mm. Average width 14.1 mm. Average thickness 7.6 mm. Average weight 1.3 gm, varies slightly with fertility of the soil and climatic conditions.

*Form.*—Ovate.

*Shape.*–Slightly thick to flat, elongated. Base rounded. Apex acuminate, slight point, average 0.3 mm.

*Surface texture.*—Slightly wrinkled on some kernels, otherwise smooth, similar to 'Nonpariel' Almond (non-patented).

*Pellicle.*—Medium size.

*Color.*—Varies from 10YR 7/8 to 10YR 6/8.

*Number of doubles.*—Low, usually less than 10%. Varies slightly with fertility, climatic conditions and cultural practices.

*Flavor.*—Good, sweet.

*Quality.*—Very good.

Use: Market— local and long distance.

Keeping quality: Good, will store for 1 year with no breakdown of kernel in appearance or flavor.

Shipping quality: Good, comparable to 'Nonpariel' Almond (non-patented).

Plant/fruit disease resistance/susceptibility: No specific testing for relative plant/fruit disease resistance/susceptibility has been designed. Under close observation during planting, growing and harvesting of nuts, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific almond tree, its flowers, foliage and nuts herein described may vary in slight detail due to climate, soil conditions, and cultural practices under which the variety may be grown. The present description is that of the variety grown under the ecological conditions prevailing near Modesto, Calif.

It is claimed:

1. A new and distinct variety of Interspecific Almond tree, substantially as illustrated and described.

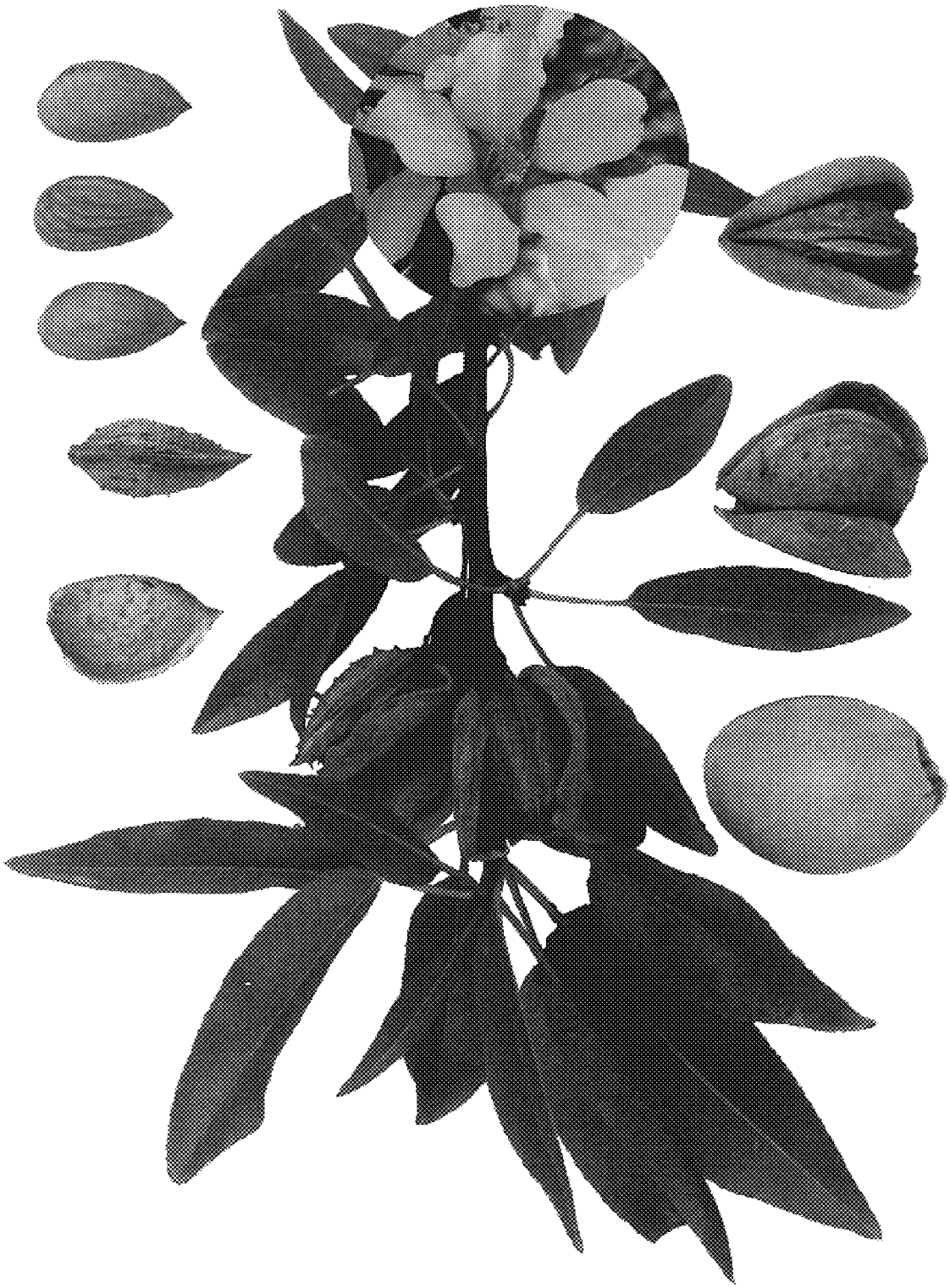

* * * * *